US012765855B2

(12) United States Patent
Hoelzer

(10) Patent No.: US 12,765,855 B2
(45) Date of Patent: Oct. 20, 2026

(54) METHOD OF PERFORMING LUNG NODULE ASSESSMENT

(71) Applicant: Siemens Healthineers AG, Forchheim (DE)

(72) Inventor: Philipp Hoelzer, Bubenreuth (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 619 days.

(21) Appl. No.: 18/168,295

(22) Filed: Feb. 13, 2023

(65) Prior Publication Data

US 2023/0255582 A1 Aug. 17, 2023

(30) Foreign Application Priority Data

Feb. 15, 2022 (EP) .................................... 22156808
May 6, 2022 (EP) .................................... 22171977

(51) Int. Cl.
*A61B 6/00* (2024.01)
*G01N 33/5752* (2026.01)
(Continued)

(52) U.S. Cl.
CPC ....... *A61B 6/5217* (2013.01); *G01N 33/5752* (2026.01); *G06N 3/09* (2023.01);
(Continued)

(58) Field of Classification Search
CPC ............ A61B 6/5217; G01N 33/57423; G06T 7/0012; G06T 7/0016; G06T 2207/10081;
(Continued)

(56) References Cited

U.S. PATENT DOCUMENTS 11,107,572 B1 * 8/2021 Ganeshananthan .... G16H 30/20
2003/0018245 A1 1/2003 Kaufman et al.
(Continued)

FOREIGN PATENT DOCUMENTS

CN 108549912 A 9/2018
CN 109711315 A 5/2019
(Continued)

OTHER PUBLICATIONS

Chen et al., "LDNNET: Towards Robust Classification of Lung Nodule and Cancer Using Lung Dense Neural Network", IEEE Access, vol. 9, 2021, pp. 50301-50320. (Year: 2021).*
(Continued)

*Primary Examiner* — Jennifer Mehmood
*Assistant Examiner* — Jose M Torres
(74) *Attorney, Agent, or Firm* — Harness, Dickey & Pierce, P.L.C.

(57) ABSTRACT

One or more example embodiments describes a method of performing lung nodule assessment, which method comprises the steps of obtaining a lung scan for a patient from an imaging modality; obtaining a blood panel for that patient from a blood analysis modality; and processing the lung scan and the blood panel in a classifier, which classifier is trained to assess a lung nodule based on the lung scan and the blood panel. The invention further describes a method of training such a classifier, and a lung nodule assessment arrangement.

17 Claims, 3 Drawing Sheets

(51) Int. Cl.

| | |
|---|---|
| ***G06N 3/09*** | (2023.01) |
| ***G06T 7/00*** | (2017.01) |
| ***G06V 10/764*** | (2022.01) |
| ***G16H 10/40*** | (2018.01) |
| ***G16H 30/40*** | (2018.01) |
| ***G16H 50/20*** | (2018.01) |
| ***G16H 50/30*** | (2018.01) |

(52) U.S. Cl.
CPC .......... *G06T 7/0012* (2013.01); *G06T 7/0016* (2013.01); *G06V 10/764* (2022.01); *G16H 10/40* (2018.01); *G16H 30/40* (2018.01); *G16H 50/20* (2018.01); *G16H 50/30* (2018.01); *G06T 2207/10081* (2013.01); *G06T 2207/10116* (2013.01); *G06T 2207/20081* (2013.01); *G06T 2207/20084* (2013.01); *G06T 2207/30064* (2013.01)

(58) Field of Classification Search
CPC . G06T 2207/10116; G06T 2207/20081; G06T 2207/20084; G06T 2207/30064; G16H 10/40; G16H 30/40; G16H 50/20; G16H 50/30; G06N 3/09; G06V 10/764
See application file for complete search history.

(56) References Cited

U.S. PATENT DOCUMENTS

| | | | | |
|---|---|---|---|---|
| 2004/0252870 | A1* | 12/2004 | Reeves | G06T 7/136 382/128 |
| 2005/0207630 | A1* | 9/2005 | Chan | G06T 7/0012 382/131 |
| 2010/0111386 | A1* | 5/2010 | El-Baz | G06T 7/143 382/128 |
| 2015/0185204 | A1* | 7/2015 | Kuhn | G01N 33/5005 424/1.73 |
| 2018/0059113 | A1 | 3/2018 | Kearney et al. | |
| 2018/0204645 | A1* | 7/2018 | El Saadawi | G16H 50/70 |
| 2019/0131016 | A1 | 5/2019 | Cohen et al. | |
| 2019/0180153 | A1* | 6/2019 | Buckler | G06F 18/29 |
| 2019/0183429 | A1* | 6/2019 | Sung | A61B 5/7267 |
| 2020/0005901 | A1* | 1/2020 | Cohen | G16B 40/20 |
| 2020/0160997 | A1* | 5/2020 | Bagci | A61B 5/055 |
| 2020/0405225 | A1* | 12/2020 | Kennedy | A61B 5/4842 |
| 2021/0256323 | A1 | 8/2021 | Hinnant et al. | |
| 2022/0148733 | A1* | 5/2022 | Arteta | G16H 50/30 |
| 2022/0180514 | A1* | 6/2022 | Vlasimsky | A61B 6/50 |
| 2022/0327690 | A1* | 10/2022 | Waterfield Price | G16H 50/20 |
| 2023/0094690 | A1* | 3/2023 | Sharma | G16H 70/20 705/2 |
| 2024/0071622 | A1* | 2/2024 | Kennedy | C12Q 1/6886 |
| 2025/0014755 | A1* | 1/2025 | Young | G16H 15/00 |

FOREIGN PATENT DOCUMENTS

| | | | |
|---|---|---|---|
| CN | 111833330 | A | 10/2020 |
| CN | 112382392 | A | 2/2021 |
| CN | 112686343 | A | 4/2021 |
| CN | 113160883 | A | 7/2021 |

OTHER PUBLICATIONS

Rafael-Palou et al., "Detection, Growth Quantification and Malignancy Prediction of Pulmonary Nodules Using Deep Convolutional Networks in Follow-up CT Scans", arXiv:2103.14537, 2021, pp. 1-25. (Year: 2021).*

MacMahon et al., "Guidelines for Management of Incidental Pulmonary Nodules Detected on CT Images: From the Fleischner Society 2017", Radiology: vol. 284: No. 1, Jul. 2017, pp. 1-16. (Year: 2017).*

Madero Orozco et al., "Automated system for lung nodules classification based on wavelet feature descriptor and support vector machine", BioMedical Engineering OnLine (2015) 14:9, pp. 1-20. (Year: 2015).*

Kourou et al. "Machine learning applications in cancer prognosis and prediction", Computational and Structural Biotechnology Journal, vol. 13, 2015, pp. 8-17.

Wang Weilun et al: "Evaluation of Malignancy of Lung Nodules from CT Image Using Recurrent Neural Network", 2019 IEEE International Conference On Systems, Man and Cybernetics (SMC), IEEE, Oct. 6, 2019 (Oct. 6, 2019), pp. 2992-2997, XP033667478, DOI: 10.1109/SMC.2019.8913885 [retrieved on Nov. 26, 2019].

Massion et al., "Autoantibody signature enhances the positive predictive power of computed tomography and nodule-based risk models for detection of lung cancer", J. Thor. Onc. 12 (2017) 578-584.

* cited by examiner

METHOD OF PERFORMING LUNG NODULE ASSESSMENT

CROSS-REFERENCE TO RELATED APPLICATION(S)

The present application claims priority under 35 U.S.C. § 119 to European Patent Application No. 22156808.2, filed Feb. 15, 2022 and European Patent Application No. 22171977.6, filed May 6, 2022, the entire contents of each of which are incorporated herein by reference.

RELATED ART

It is important to detect lung cancer at an early stage in order for the patient to be treated successfully. When caught early, the prospects of curing lung cancer are considerably higher than at a later stage. Lung cancer can develop from a lung nodule, which may be visible in a lung scan such as a 2D X-ray image, a 3D computed tomography scan, or any scan obtained using techniques such as magnetic resonance imaging, ultrasound, photoacoustic tomography, diffusion-weighted tomography, positron emission tomography, etc.

However, numerous other maladies may also result in the formation of lung nodules. For example, lung nodules may result from mycobacterial infection, fungal infection, round pneumonia, lung abscess, septic emboli, nocardia infection, hydatid cyst or echinococcosis, Q fever from *Coxiella burnetii*, etc. Lung nodules may also arise from immune system disorders such as rheumatoid arthritis, granulomatosis with polyangiitis, nodular sarcoidosis, organizing pneumonia (cryptogenic or secondary), lymphoid granulomatosis, necrotizing sarcoid granulomatosis. Further causes of lung nodules may be congenital abnormalities such as arteriovenous malformation, bronchogenic cysts, pulmonary sequestration, pulmonary venous varix, bronchial atresia with bronchocele; future causes may be rounded atelectasis, endoparenchymal lymph node, progressive mass fibrosis, inflammatory pseudotumor, amyloidosis, lipoid pneumonia, etc.

A pulmonary nodule or lung nodule can be detected in a lung scan such as an X-ray image or a CT image. However, benign nodules are similar in appearance to malignant nodules. It is known to estimate an image-based malignancy score or “risk score” for a pulmonary nodule under consideration of further information about the patient, for example the patient’s age, smoking history, etc. Examples of such approaches are the Mayo/Swensen model, the Brock model and the VA (Veterans Administration) model. However, the overwhelming majority of detected pulmonary nodules (80-95%) is benign, so that the estimated risk score is frequently incorrect. In an effort to improve pulmonary nodule classification, it is known to combine image marker information (e.g. markers or features identified from a CT lung scan) and blood marker information (e.g. markers or features such as genomic, epigenomic, transcriptomic, metabolomic or proteomic markers identified in a blood test or blood panel) to obtain a more accurate risk score. However, the accuracy of the known techniques depends on the relevance of the blood marker data as well as on the clinician’s ability to evaluate the additional information in the context of the lung nodule. Even with this combined approach, the rate of misdiagnosis is still unacceptably high, leading to false positive diagnosis, but also false negative diagnosis.

A false-positive misdiagnosis (a high risk score is assigned to a lung nodule) often results in follow-up treatment for the patient with further costs, additional exposure to radiation, and possibly also surgical complications. In addition to the significant costs of unnecessary treatment, the patient may needlessly suffer from psychological anxiety. A false-negative misdiagnosis (a low risk score is assigned to a lung nodule) can mean that early-stage lung cancer remains undetected, and this may result in a significantly worse outlook for the patient, particularly for a patient not participating in a regular screening program.

Artificial intelligence (AI) can be applied to analyse vast quantities of data in order to identify relationships that would otherwise be difficult or impossible to detect using conventional “manual” techniques. For example, an AI classifier can be trained to recognise certain type of pattern in input data. A classifier can be realised in various ways, for example as a decision tree, a support-vector machine, a Bayes classifier, a neural network, etc. It is known to use AI to analyse lung scans in order to identify lung nodules.

SUMMARY

However, because a “harmless” lung nodule is often visually indistinguishable from a malignant carcinoma, the clinical usefulness of such an approach is limited.

One or more example embodiments of the present invention improve the accuracy of pulmonary nodule classification.

According to one or more example embodiments of the present invention, a method of performing lung nodule assessment comprises the steps of obtaining a lung scan of a patient from an imaging modality; obtaining a blood panel for that patient; processing the lung scan and the blood panel in an AI classifier such as a residual neural network (ResNet), a convolutional neural network, a Bayes classifier, etc. The classifier is trained to assess a lung nodule on the basis of the lung scan and the blood panel and to output the results of the classification in a meaningful manner, for example as a cancer risk score, as a probability of malignancy, etc.

According to one or more example embodiments, the processing includes identifying a number of image markers from the lung scan, an image marker comprising at least one of:

a vascular convergence;
a pleural indentation;
an air bronchogram;
a calcification type;
a cavitation; endobronchial origin;
a perifissural location;
a subpleural location;
a morphology;
a spiculation;
a lobulation;
an associated cystic airspace; or
bubble-like lucencies in the lung nodule.

According to one or more example embodiments, the processing includes identifying a number of blood markers from the blood panel using the classifier, a blood marker comprising at least one of a genomic marker, an epigenomic marker, a transcriptomic marker, a metabolomics marker, or a proteomic marker.

According to one or more example embodiments, the processing includes identifying a relationship between an image marker and a respiratory disease using the classifier.

According to one or more example embodiments, the processing includes identifying a discrepancy between the lung scan and an older lung scan of the patient using the classifier.

According to one or more example embodiments, the classifier is configured to at least one of compare a volume of a specific region in the lung scan to a volume of the same region in the older lung scan, or quantify an indolence of the lung nodule identified in the lung scan.

According to one or more example embodiments, coefficients of the classifier are based on a context of the obtaining the lung scan.

According to one or more example embodiments, the processing includes proposing a patient management procedure based on the lung nodule assessment.

According to one or more example embodiments, the classifier is trained to perform lung nodule assessment also based on extrapulmonary image data, and wherein the method comprises preparing for obtaining extrapulmonary image data.

According to one or more example embodiments, a method of training a classifier includes (A) annotating a lung scan to identify a lung nodule and a number of image markers associated with the lung nodule; (B) annotating a blood panel to identify a number of blood markers associated with lung cancer; (C) determining an assessment for the lung nodule for use as a ground truth by the classifier; (D) applying the classifier to the lung scan, the blood panel and the associated ground truth; and repeating steps A-D until a desired level of accuracy has been achieved.

According to one or more example embodiments, the classifier is trained with at least 100 datasets, wherein a dataset comprises at least one lung scan of a patient and at least one blood panel for that patient.

According to one or more example embodiments, the classifier is trained with a first training cohort and a second training cohort, the first training cohort including datasets comprising lung scans obtained from lung cancer screening procedures, and the second training cohort including datasets comprising lung scans obtained incidentally.

According to one or more example embodiments, a lung nodule assessment arrangement includes an imaging modality configured to provide a lung scan of a patient; a blood analysis modality configured to provide a blood panel for that patient; a processing unit configured to a method according to one or more example embodiments; and a user interface configured at least to display the lung nodule assessment in a context of the lung scan.

According to one or more example embodiments, a non-transitory computer program product comprises a computer program that, when executed by a control unit, causes the control unit to perform a method according to one or more example embodiments.

According to one or more example embodiments, a non-transitory computer-readable medium includes program elements that, when executed by a computer unit, causes the computer unit to perform a method according to one or more example embodiments.

BRIEF DESCRIPTION OF THE DRAWINGS

Other objects and features of example embodiments of the present invention will become apparent from the following detailed descriptions considered in conjunction with the accompanying drawings. It is to be understood, however, that the drawings are designed solely for the purposes of illustration and not as a definition of the limits of the invention.

In the diagrams, like numbers refer to like objects throughout. Objects in the diagrams are not necessarily drawn to scale.

DETAILED DESCRIPTION

Figure 1:
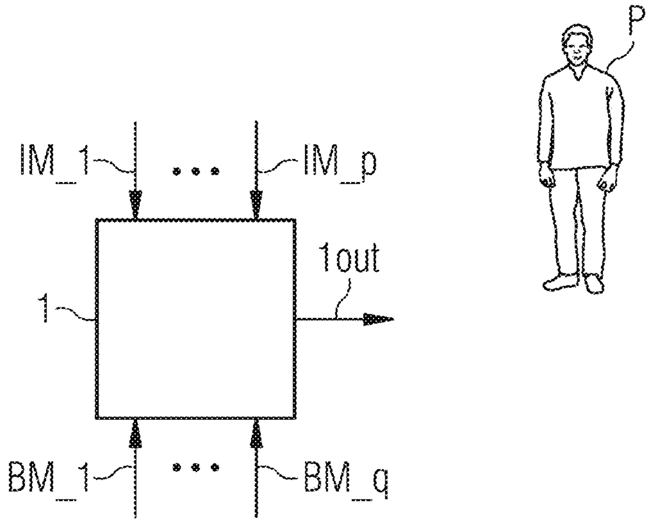
FIG. 1 is a simplified block diagram illustrating one or more example embodiments of the present invention.

A lung scan (or "pulmonary scan") can be a 2D image such as an X-ray of the chest cavity, a 3D image such as pulmonary CT (computed tomography) scan, etc. The terms "lung scan" and "pulmonary scan" are synonyms and are used interchangeably herein. Similarly, the terms "lung nodule" and "pulmonary nodule" are used interchangeably.

As explained above, a lung nodule may indicate cancer but may equally well be related to a non-cancer disorder, i.e. lung nodules are often indeterminate. The inventive method combines imaging information and laboratory diagnostic information to manage indeterminate pulmonary nodules, i.e. to arrive at a reliable assessment (e.g. a risk score) for a pulmonary nodule. An advantage of the inventive method is that it reliably distinguishes between benign and malignant lung nodules. By applying machine learning, an AI classifier is able to identify information in the lung scan and blood panel and to combine this information to arrive at an accurate assessment of the lung nodule.

According to one or more example embodiments of the present invention, the method of training a classifier for use in an inventive lung nodule assessment method comprises the steps of A) annotating a lung scan to identify a lung nodule and a number of image markers associated with the lung nodule;

B) annotating a blood panel to identify a number of blood markers associated with lung cancer;

C) determining an assessment for the lung nodule for use as a ground truth by the classifier;

D) applying the classifier to the lung scan, the blood panel and the associated ground truth; and repeating steps A-D until a desired level of accuracy has been achieved.

According to one or more example embodiments of the present invention, the lung nodule assessment arrangement comprises an imaging module configured to provide a lung scan of a patient; a blood analyser configured to provide a blood panel for that patient; a processing unit configured to perform steps of the lung nodule assessment method when the classifier trained according to the inventive training method loaded into a memory of the processing unit; and a user interface configured at least to display the lung nodule assessment result. The "lung nodule assessment method" may simply be referred to as the "assessment method" in the following.

One or more example embodiments of the present invention also includes a computer program product comprising a computer program that is directly loadable into a memory of a control unit of a lung nodule assessment arrangement and which comprises program elements for performing steps of the inventive lung nodule assessment method when the computer program is executed by the control unit.

One or more example embodiments of the present invention also includes a computer-readable medium on which is stored program elements that can be read and executed by a computer unit in order to perform steps of the inventive lung nodule assessment method when the program elements are executed by the computer unit.

Particularly advantageous embodiments and features of the invention are given by the dependent claims, as revealed in the following description. Features of different claim categories may be combined as appropriate to give further embodiments not described herein.

In the following, it may be assumed that the lung scan is obtained from a high-resolution imaging apparatus such as a CT scanner. A blood panel can be provided in the form of a machine-readable file, for example by a laboratory equipped to analyse blood samples. The lung scan and blood panel are preferably obtained at about the same time, for example within a few weeks.

The classifier is trained with a training cohort preferably comprising at least 100 datasets, more preferably comprising at least 1,000 datasets, most preferably comprising at least 10,000 datasets. A dataset shall be understood to comprise at least one lung scan of a patient and at least one blood panel for that patient. A training dataset can also comprise one or more older lung scans and one or more older blood scans for the same patient.

The methodology for processing an input dataset is explained in the following: trained personnel such as radiologists or other clinicians examine images obtained from lung scans (e.g. CT, MRI, ultrasound, photoacoustic tomography, diffusion-weighted tomography, positron emission tomography scans) to identify lung nodules. Any lung nodule visible in an image is annotated in a suitable manner, e.g. a contour can be drawn about the nodule in each image of a sequence (in the case of a 3D image such as a CT scan). The clinician preferably also provides additional annotations regarding the aetiology of the nodule, for example "nodule is a carcinoma", "lung nodule is a hydatid cyst", etc. A global annotation such as "nodule is malignant" or "nodule is benign" is also preferably added. In a similar fashion, annotations are added to the blood panel accompanying each lung scan. Relevant blood markers may be protein markers (hormones, enzymes, antibodies), genomic markers, epigenomic markers, transcript RNA markers, microbiomic markers, etc. An annotation is preferably made for each blood marker that is above or below a critical threshold, i.e. a threshold that is critical in the context of lung cancer.

This step of annotating the image data and blood panel converts the datasets into training data that is relevant to the objective of assessing the nature of a lung nodule in terms of its aetiology and severity. For each dataset, the clinician can formulate an assessment for the lung nodule visible in the image data, for example a risk score, a malignancy probability, etc. This assessment is a ground truth for the classifier.

A lung nodule can appear as a small dark region within the lung. Various characteristics can be relevant in the assessment of its nature. Therefore, in a preferred embodiment of the invention, the classifier is configured to extract or retrieve a number of image markers from the lung scan. An image marker can comprise any of: vascular convergence; pleural indentation; air bronchogram; calcification type; cavitation; endobronchial origin; perifissural location; subpleural location; morphology; spiculation, lobulation, associated cystic airspace, bubble-like lucencies in a nodule. Preferably, the classifier is configured to perform image segmentation, for example semantic or context-driven image segmentation, to identify any such image markers in the lung scan.

It is known that certain pulmonary comorbidities such as COPD (chronic obstructive pulmonary disease) increase the risk of developing lung cancer. Therefore, in a particularly preferred embodiment of the invention, the classifier automatically identifies image markers associated with a respiratory disease such as emphysema, airway inflammation, pleural effusion, interstitial lung disease, infections, vascular disease, etc. The number of identified image markers and the relevance of each image marker can be used by the classifier to arrive at a more precise risk score for a lung nodule.

In a patient with lung cancer, physical changes may be observed to the lung over time. An early indicator of pulmonary disease is a reduction in size of a pulmonary volume such as lobar volume or a segmental volumes. Therefore, in a further preferred embodiment of the invention, the classifier is configured to identify a discrepancy between the current lung scan and an older lung scan of that patient. Particularly in the case of a patient participating in a lung cancer screening program, multiple older lung scans may be available for that patient. For example, the classifier may be configured to determine the volume of a specific pulmonary region in the most recent lung scan, to determine the volume of the same pulmonary region in one or more older lung scans for the same patient, and to compare the results. Any reduction in lung volume over time can be included by the classifier in its assessment of a lung nodule.

A lung nodule can be detected incidentally, for example, a lung nodule may be noticed in a CT image generated for a different reason, for example to assess injury following an accident. Alternatively, a lung nodule made be identified in the course of a lung cancer screening program. The probability for cancer is somewhat different in both scenarios, since a patient that participates in a cancer screening program generally already carries a higher risk of developing cancer. Screening-compliant patients can have annual scans, thereby reducing the risk of missing cancer as it can still be detected on the next scan. In contrast, incidentally found lung nodules may be followed by a more aggressive patient management approach in some countries, since the patient might not undergo further scanning. In such cases, the correct assessment of an incidentally-discovered lung nodule is very important because any decision to rule out cancer has to be made with high degree of certainty. Therefore, in a particularly preferred embodiment of the invention, the classifier is trained with a first training cohort in which the datasets are obtained from participants in lung cancer screening procedures; and with a second training cohort in which the datasets are obtained from patients undergoing incidental lung scans. This "two-pronged" training allows the classifier to be configured in a context-specific manner in order to deal with these different scenarios. For example, the classifier can have slightly different operating points or decision thresholds for "screening nodules" and "incidental nodules", i.e. any decision thresholds for a lung nodule identified in the course of a screening program may differ slightly from decision thresholds for a lung nodule identified incidentally.

It is known that certain biomarkers, for example certain blood markers, are elevated in only some types of lung cancer, possibly only in the case of one specific type of lung cancer. Furthermore, it is known that nodules resulting from different types of lung cancer develop in specific locations within the lung. For example, lung nodules associated with some types of lung cancer develop in central locations, while nodules associated with other types of lung cancer develop in peripheral locations. Therefore, in a further preferred embodiment of the invention, classifier is configured to identify the type of cancer associated with a lung nodule detected in the lung scan. For example, the classifier can be configured to determine whether the lung nodule is indicative of small-cell carcinoma, adenocarcinoma, squamous cell carcinoma, large cell carcinoma, etc.

Some blood markers such as autoantibodies are not specific to lung cancer but may also be elevated in the case of other non-pulmonary cancers such as prostate cancer, gastric cancer, liver cancer, testicular cancer, breast cancer, colorectal cancer, etc. Furthermore, such blood markers may also be elevated in a patient with an autoimmune disease. Therefore, in a particularly preferred embodiment of the invention, the classifier is trained to perform lung nodule evaluation also on the basis of extrapulmonary image data. In addition to current lung scan(s) and blood panel(s) for each patient, a training dataset can also comprise one or more extrapulmonary scans. The inventive lung nodule assessment method preferably comprises a preparatory step of obtaining extrapulmonary image data. For example, image markers from a mammography may indicate an advanced stage of breast cancer, and it may be assumed that the lung nodule is not the cause of the elevated blood markers. Equally, the risk score of a lung nodule may be higher if the image markers of a mammography indicate only a very minor lesion. In this way, the classifier is trained and configured to assess a lung nodule not only in the context of imaging markers from the lung scan and blood markers from a blood panel, but also in the context of markers from extrapulmonary images. An advantage is that the specificity and assessment accuracy of the inventive method can be favourably high.

The lung nodule assessment method may conclude with a report stating the outcome. For example, if the classifier has detected a lung nodule in the lung scan, it may report a risk score for that lung nodule. The risk score can be a Solitary Pulmonary Nodule (SPN) malignancy risk score based on the Mayo Clinic Model, on the Bayesian Inference Malignancy Calculator, or any such well-established model. A suitable approach to patient management may depend on the risk score, on the probable nature of the carcinoma, on other illnesses of the patient, etc. Therefore, in a preferred embodiment of the invention, the classifier may also report the cancer type associated with the lung nodule, for example in terms of probability. In a preferred embodiment of the invention, the classifier proposes a suitable patient management procedure on the basis of the lung nodule assessment, for example to schedule a biopsy, a PET scan, CT surveillance, etc. If adjuvant radiation treatment or preventive radiation treatment is proposed, the classifier may also compute a suitable Gray dose for a specific lung nodule. These various types of information can form part of a report that is generated for the clinician or user.

A lung nodule seen in an image can be characterized by various features such as its location, degree of vascular convergence, degree of pleural indentation, etc. Manual determination of such features or image markers can be tedious and error-prone. Therefore, in a particularly preferred embodiment of the invention, the classifier automatically identifies or retrieves less dominant malignant nodule image markers or features such as vascular convergence, pleural indentation, air bronchograms, types of calcifications, cavitation, endobronchial origin, perifissural location, subpleural location, etc.

The prior art approaches primarily strive to quantify the malignancy of a lung nodule and to express this as the risk score. However, it is known that a certain proportion of lung cancers is found post-mortem, i.e. such patients died not because of lung cancer, but with lung cancer. It is possible for such a patient to have had lung cancer with one or more nodules that grow only slowly, i.e. the nodules are indolent. Therefore, in a further preferred embodiment of the invention, the classifier quantifies the indolence of a lung nodule and includes the lung nodule indolence in computation of the risk score.

For example, the classifier can be trained with outcome data indicative of the level of aggressiveness. To this end, the rate of growth of a nodule can be determined by comparing annual lung scans of the same patient.

In a further preferred embodiment of the invention, outcome data is determined and provided to the classifier. For example, in the case of an aggressive nodule, the patient outcome and/or the degree of metastasis may be known. Such outcome data is preferably used in the training stage of the classifier. In this way, the inventive lung assessment arrangement can assist in deciding whether or not aggressive management is appropriate for a patient with an indolent (malignant but slow-growing) lung nodule. Under consideration of the relevant factors such as the measure of indolence, the patient's age, degree of metastasis etc., a more favourable approach to treatment may be established. By also including an assessment of the indolence of a lung nodule, the inventive assessment method has a significantly higher clinical utility than the prior art approaches.

FIG. 1 is a simplified block diagram illustrating one or more example embodiments of the present invention. The diagram shows an AI classifier 1 such as a deep learning neural network, a Bayes classifier, a decision tree, etc. The classifier 1 receives a plurality of image markers IM_1, . . . , IM_p and a plurality of blood markers BM_1, . . . , BM_p. The image markers IM_1, . . . , IM_p are obtained from a lung scan for a patient P. A clinician may already have identified a nodule in the lung scan. The blood markers BM_1, . . . , BM_p are obtained from analysis of a blood panel resulting from a blood sample of the same patient P. The classifier 1 has been trained to arrive at a diagnosis or assessment 1out. The assessment 1out can be in the form of a risk score, for example. In the case of a high risk score, i.e. the classifier 1 has concluded that a lung nodule is probably indicative of cancer, the assessment 1out may also include the likelihood of the lung nodule being related to a certain cancer type. The assessment 1out may be in the form of a more extensive report, and may also include a proposed cancer management plan for the patient if the risk score is above a certain threshold.

Figure 2:
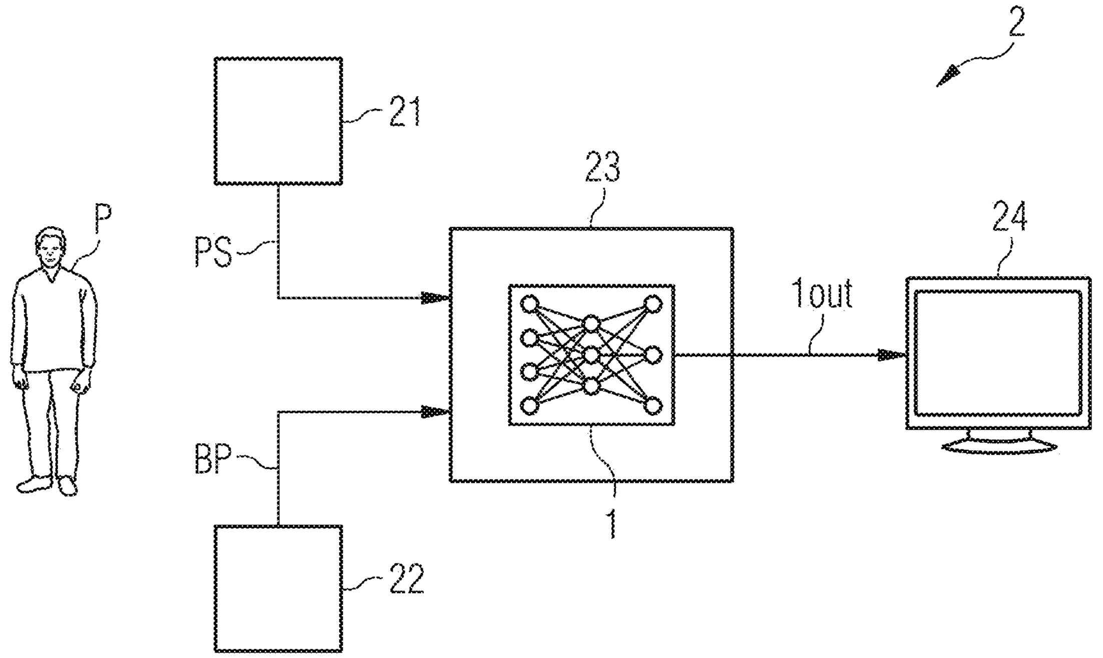
FIG. 2 is a simplified block diagram of an exemplary embodiment of a lung nodule assessment arrangement.

FIG. 2 shows a simplified block diagram of an exemplary embodiment of the inventive lung nodule assessment arrangement 2, and shows an imaging modality 21 configured to provide a pulmonary scan PS of a patient P, and a blood analysis means 22 (blood analysis modality) for providing a blood panel BP for that patient P. The blood analysis means 22 may be a known blood analyzer such as an immunoassay analyzer, a tumor marker analyzer and/or a chemistry analyzer.

An immunoassay analyzer can measure levels of specific proteins, such as carcinoembryonic antigen (CEA) and cytokeratin fragment 21-1 (CYFRA 21-1), that are often elevated in individuals with lung cancer. A tumor marker analyzer is configured to measure levels of biomarkers that are associated with cancer, including CEA, CYFRA 21-1 and others. A chemistry analyzer can measure levels of substances in blood that may indicate a presence of lung cancer, such as lactate dehydrogenase (LDH) and alkaline phosphate (ALP). The lung nodule assessment arrangement 2 also comprises a processing unit 23 configured to perform steps of the method according to any of claims 1 to 9 when the trained classifier 1 is loaded into a memory of the processing unit. A user interface 24 is configured to display the lung nodule assessment result 1out in the context of the pulmonary scan PS.

Figure 3:
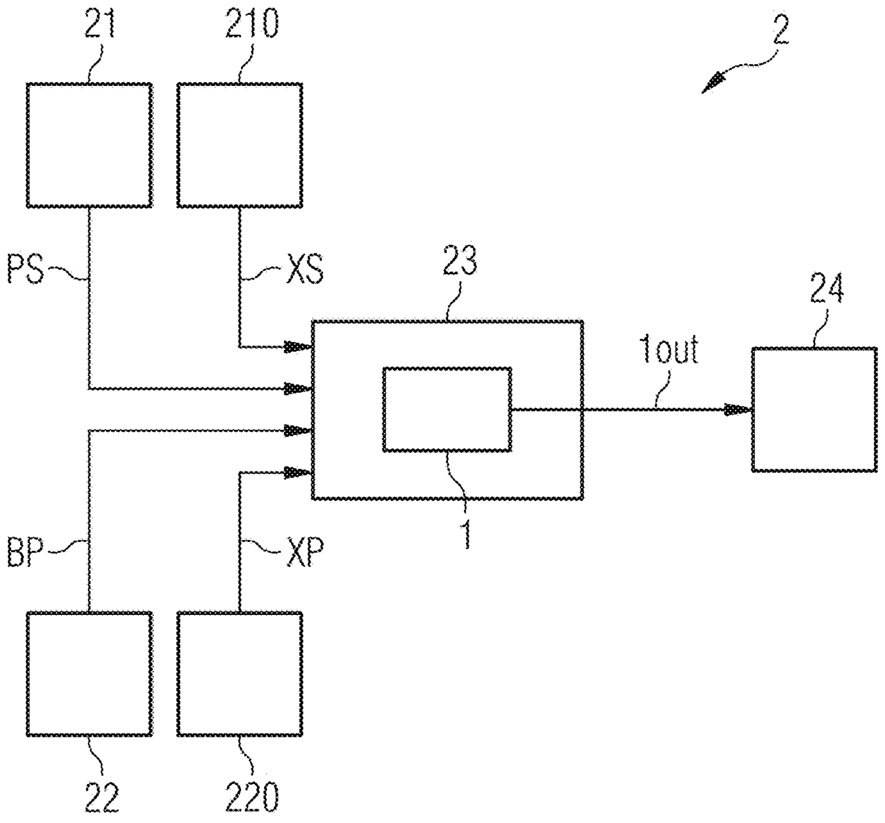
FIG. 3 is a simplified block diagram of a further embodiment of a lung nodule assessment arrangement.

FIG. 3 shows a simplified block diagram of another embodiment of the inventive lung nodule assessment arrangement 2. In addition to the pulmonary scan PS obtained from the imaging modality 21, an extrapulmonary scan XS may be obtained from a further imaging modality 210. In addition to the blood panel BP, a further set of biomarkers, e.g. salivary biomarkers, volatile organic compound (VOC) biomarkers from exhaled breath, urine biomarkers, stool biomarkers etc. may be obtained from a further biomarker modality 220. The trained classifier 1 processes the biomarkers from each source to arrive at an assessment for a lung nodule in the pulmonary scan PS. Here also, a user interface 24 displays the assessment result 1out in the context of the pulmonary scan PS.

Figure 4:
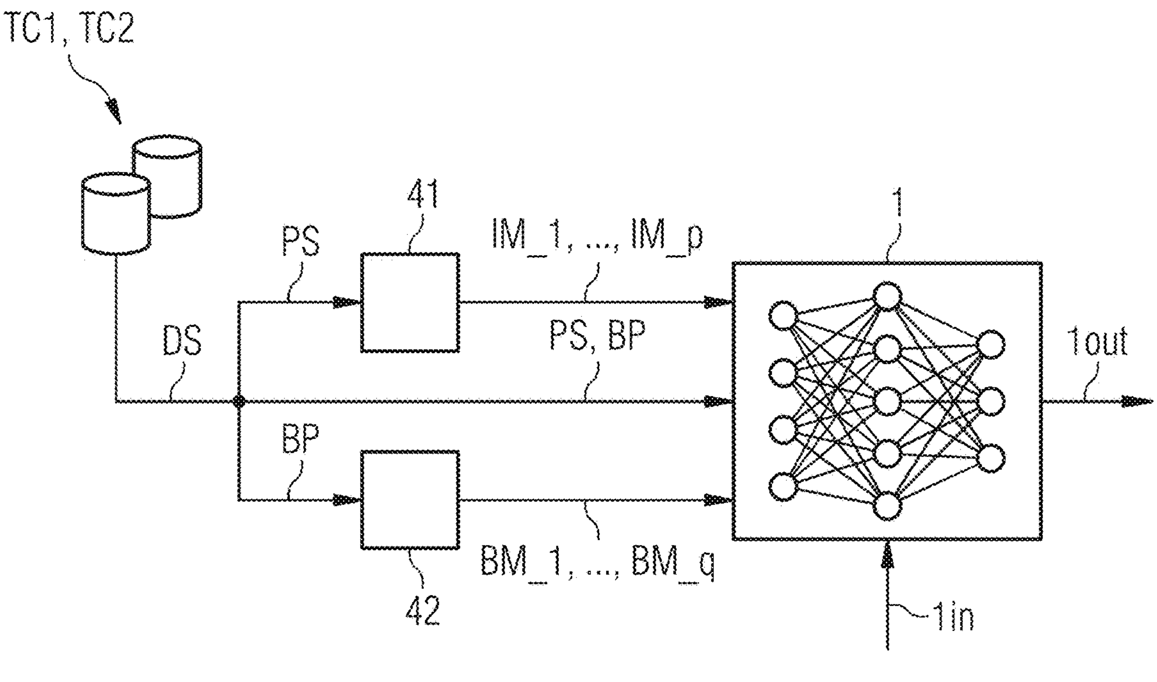
FIG. 4 illustrates a training stage of the classifier of a lung nodule assessment arrangement according to one or more example embodiments of the present invention.

The skilled person can be expected to choose a suitable classifier with the aim of processing image data and blood panel data, and can be assumed to be familiar with the procedure of training such a classifier. FIG. 4 illustrates an exemplary training procedure for the classifier 1 of FIGS. 1-3. The classifier 1 in this exemplary embodiment is a neural network, illustrated in the conventional manner with an input layer, hidden layer and output layer each comprising a number of nodes. The nodes are connected according to coefficients or weights.

A dataset DS is provided, comprising a pulmonary scan PS and a blood panel BP of a specific patient. Both the pulmonary scan PS and the blood panel BP are annotated by experienced personnel to identify (in stage 41) image markers IM_1, . . . , IM_p relevant to a lung nodule present in the pulmonary scan and to identify (in stage 42) blood markers BM_1, . . . , BM_p relevant to lung cancer. For example, a clinician can determine image markers regarding the size, position and morphology of a lung nodule, and can also identify relevant elevations of proteins in the blood panel. The clinician computes an expected risk score for that lung nodule. Other relevant markers present in the dataset—for example patient's age, gender, smoking history, comorbidities etc.—are also included in the annotated dataset fed into the classifier 1. The clinician's assessment, e.g. an estimated risk score for the lung nodule, is a ground truth 1 in for the classifier. A training cohort can comprise many hundreds or even thousands of datasets. A dataset for a patient may also include lung scans taken at intervals, for example annually. A dataset for a patient may also include an electronic health record (EHR) or electronic medical record (EMR), for example. In addition to any recent lung scan and blood panel, an electronic record can comprise older lung scans as well as older blood panels, and may of course include any other type of scan, laboratory results, etc.

The annotated datasets are used to train a classifier (regression model, deep learning model, etc.) to distinguish between benign and malignant nodules, indolent and aggressive nodules, etc. The pulmonary scan PS, the blood panel BP, the markers IM_1, . . . , IM_p, BM_1, . . . , BM_p and the ground truth of each dataset are fed to the classifier 1, which learns to analyse image data and blood panel data with a view to assessing a lung nodule visible in the image data.

The classifier 1 can be trained using a single training cohort. However, more accurate and useful lung nodule assessment is obtained by training the classifier using a first training cohort TC1 comprising datasets (DS) obtained from lung cancer screening procedures, and also with a second training cohort TC2 in which the datasets DS comprise lung scans PS obtained incidentally.

Figure 5:
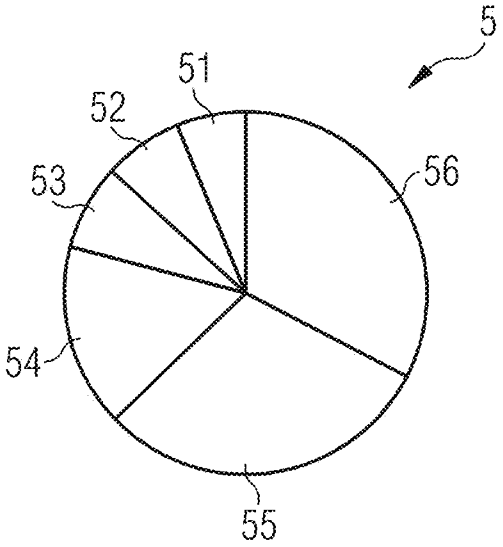
FIG. 5 illustrates factors of relevance to lung cancer.

FIG. 5 shows a pie chart 5 that illustrates the relevance of different types of risk factor when assessing a pulmonary nodule. The location of the lung nodule, the presence of spiculations, and the patient's smoking history are risk factors 51, 52, 53 respectively, each contributing 7.3%. The patient's age is a risk factor 54 that contributes 18%. The nodule size is a more relevant risk factor 55 and contributes 30%. After determining the presence of a pulmonary nodule in a lung scan, a blood test is carried out for that patient. The remaining risk factor 56 is derived from relevant blood markers, for example the levels of relevant plasma proteins such as LG3BP and C163A, and contributes the final 30%. Conventional approaches that are based on image analysis do not include data from blood tests and therefore fail to consider valuable information relating to risk factor 56 (elevation levels of relevant blood biomarkers). Similarly, an assessment approach that is based on blood panel analysis does not consider valuable information relating to risk factor 55 (nodule size).

Figure 6:
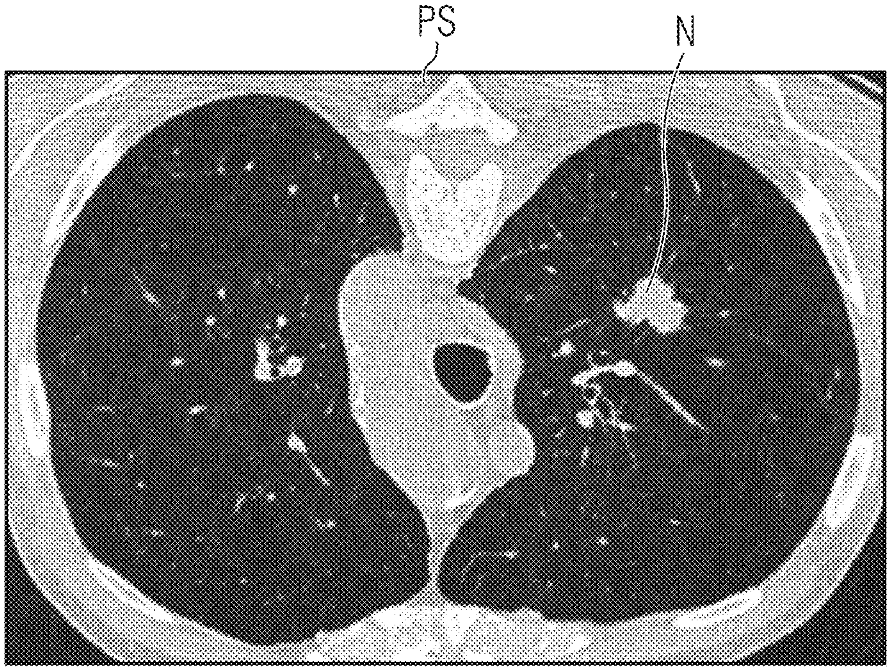
FIG. 6 is an exemplary pulmonary scan showing a lung nodule according to one or more example embodiments of the present invention.

FIG. 6 is an exemplary pulmonary scan showing a lung nodule N, which appears as a small mass. Many disorders lead to the development of benign or harmless lung nodules. However, lung cancer is always associated with the development of tumours which can start as small nodules as shown here. It is therefore very important to be able to correctly identify a lung nodule, i.e. to avoid a false negative diagnosis and also to avoid a false positive diagnosis.

Although the present invention has been disclosed in the form of preferred embodiments and variations thereon, it will be understood that numerous additional modifications and variations could be made thereto without departing from the scope of the invention.

For the sake of clarity, it is to be understood that the use of "a" or "an" throughout this application does not exclude a plurality, and "comprising" does not exclude other steps or elements. The mention of a "unit" or a "module" does not preclude the use of more than one unit or module.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein and mentioned above, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units (e.g., control unit, computer unit, processing unit) and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

The term 'module' may refer to, be part of, or include processor hardware (shared, dedicated, or group) that executes code and memory hardware (shared, dedicated, or group) that stores code executed by the processor hardware.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

The invention claimed is:

1. A method of performing lung nodule assessment, the method comprising:

obtaining a lung scan for a patient from an imaging modality;

obtaining a blood panel for the patient from a blood analysis modality; and processing the lung scan and the blood panel in a classifier, the classifier being trained to assess a lung nodule based on the lung scan and the blood panel, wherein the processing includes identifying a discrepancy between the lung scan and an older lung scan of the patient using the classifier, the classifier is configured to quantify an indolence of the lung nodule identified in the lung scan, and coefficients of the classifier are based on a context of the obtaining the lung scan, the context being whether the obtaining the lung scan is a lung cancer screening procedure or an incidental lung scan.

2. The method of claim 1, wherein the processing includes identifying a number of image markers from the lung scan, an image marker comprising at least one of:

a vascular convergence;
a pleural indentation;
an air bronchogram;
a calcification type;
a cavitation; endobronchial origin;
a perifissural location;
a subpleural location;
a morphology;
a spiculation;
a lobulation;
an associated cystic airspace; or
bubble-like lucencies in the lung nodule.

3. The method of claim 2, wherein the processing includes identifying a number of blood markers from the blood panel using the classifier, a blood marker comprising at least one of:

a genomic marker, an epigenomic marker, a transcriptomic marker, a metabolomics marker, or a proteomic marker.

4. The method of claim 3, wherein the processing includes identifying a relationship between an image marker and a respiratory disease using the classifier.

5. A non-transitory computer-readable medium including program elements that, when executed by a computer unit, cause the computer unit to perform the method of claim 2.

6. The method of claim 1, wherein the processing includes identifying a number of blood markers from the blood panel using the classifier, a blood marker comprising at least one of:

a genomic marker, an epigenomic marker, a transcriptomic marker, a metabolomics marker, or a proteomic marker.

7. The method of claim 1, wherein the processing includes identifying a relationship between an image marker and a respiratory disease using the classifier.

8. The method of claim 1, wherein the classifier is further configured to compare a volume of a specific region in the lung scan to a volume of a same region in the older lung scan.

9. The method of claim 1, wherein the processing includes proposing a patient management procedure based on the lung nodule assessment.

10. The method of claim 1, wherein the classifier is trained to perform lung nodule assessment also based on extrapulmonary image data, and wherein the method comprises:

preparing for obtaining extrapulmonary image data.

11. A lung nodule assessment arrangement comprising:

an imaging modality configured to provide a lung scan of a patient;

a blood analysis modality configured to provide a blood panel for that patient;

a processing unit configured to perform the method of claim 1; and a user interface configured at least to display the lung nodule assessment in a context of the lung scan.

12. A non-transitory computer program product comprising a computer program that, when executed by a control unit, causes the control unit to perform the method of claim 1.

13. A non-transitory computer-readable medium including program elements that, when executed by a computer unit, causes the computer unit to perform the method of claim 1.

14. The method of claim 1, wherein the classifier has different operating points or decision thresholds for lung cancer screening procedures and incidental lung scans.

15. A method of training a classifier, the method of training comprising:

(A) annotating a lung scan to identify a lung nodule and a number of image markers associated with the lung nodule;

(B) annotating a blood panel to identify a number of blood markers associated with lung cancer;

(C) determining an assessment for the lung nodule for use as a ground truth by the classifier;

(D) applying the classifier to the lung scan, the blood panel and the associated ground truth; and repeating steps A-D until a desired level of accuracy has been achieved.

16. The method of claim 15, wherein the classifier is trained with at least 100 datasets, wherein a dataset comprises at least one lung scan of a patient and at least one blood panel for that patient.

17. The method of claim 15, wherein the classifier is trained with a first training cohort and a second training cohort, the first training cohort including datasets comprising lung scans obtained from lung cancer screening procedures, and the second training cohort including datasets comprising lung scans obtained incidentally.

* * * * *